United States Patent [19]

Pereyra

[11] 4,172,458
[45] Oct. 30, 1979

[54] SURGICAL LIGATURE CARRIER

[76] Inventor: Armand J. Pereyra, 659 W. Granada Ct., Ontario, Calif. 91762

[21] Appl. No.: 848,924

[22] Filed: Nov. 7, 1977

[51] Int. Cl.² ............................................. A61B 17/06
[52] U.S. Cl. ...................................... 128/340; 128/215
[58] Field of Search .............. 128/215, 303 R, 334 R, 128/339, 340, 347

[56] References Cited

U.S. PATENT DOCUMENTS

| | | | |
|---|---|---|---|
| 2,700,385 | 1/1955 | Ortiz | 128/215 |
| 2,738,790 | 3/1956 | Todt et al. | 128/334 R |
| 2,740,404 | 4/1956 | Kohl | 128/215 |
| 2,878,809 | 3/1959 | Treace | 128/329 X |
| 3,570,498 | 3/1971 | Weighton | 128/347 |

OTHER PUBLICATIONS

Pereyra et al., Obstetrics and Gynecology, vol. 30, No. 4, Oct. 1967, pp. 537–546.

Buchsbaum et al., Gynecologic and Obstet. Urology, Chapt. 13, pp. 208–222, 1978, W. B. Saunders Co.

Primary Examiner—Dalton L. Truluck
Attorney, Agent, or Firm—Boniard I. Brown

[57] ABSTRACT

A ligature carrier for use in a suspensory-type operation known as the Revised Pereyra Procedure, which corrects prolapse of the bladder neck in women. The ligature carrier comprises an angulated needle with two aligned striated flat handles, one slidable in a brace with respect to the other to extend and retract the needle. When retracted the angulated end of the needle protrudes about 3 cm; the aligned handles provide improved control to penetrate the abdominal fascia and orient the needle thereafter. In the operation the tough fascia is so penetrated, the carrier suitably redirected, and the needle extended out through the vaginal opening by sliding the needle handle in the brace. Sutures are then threaded through the eye at the needle tip and the needle retracted.

11 Claims, 13 Drawing Figures

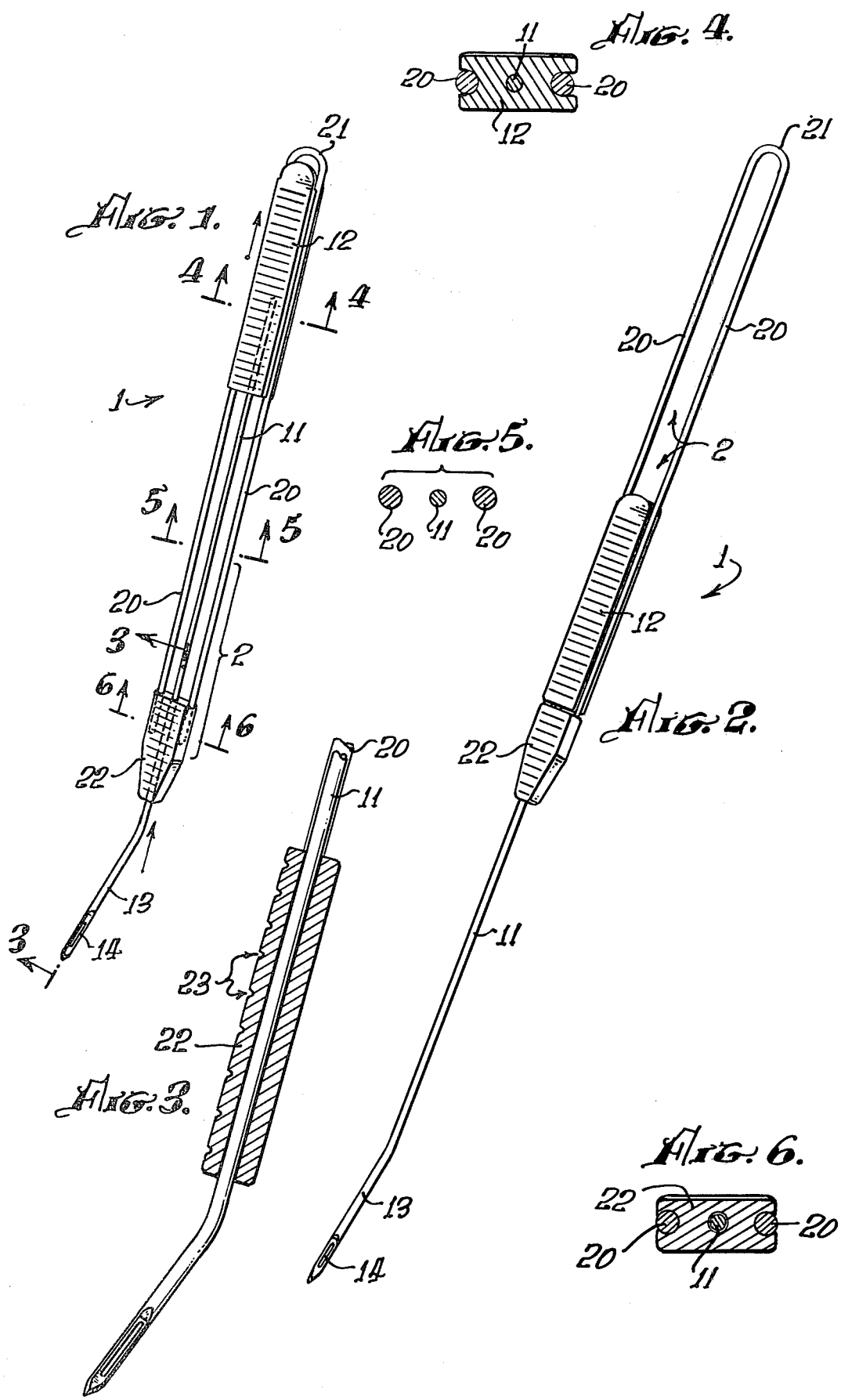

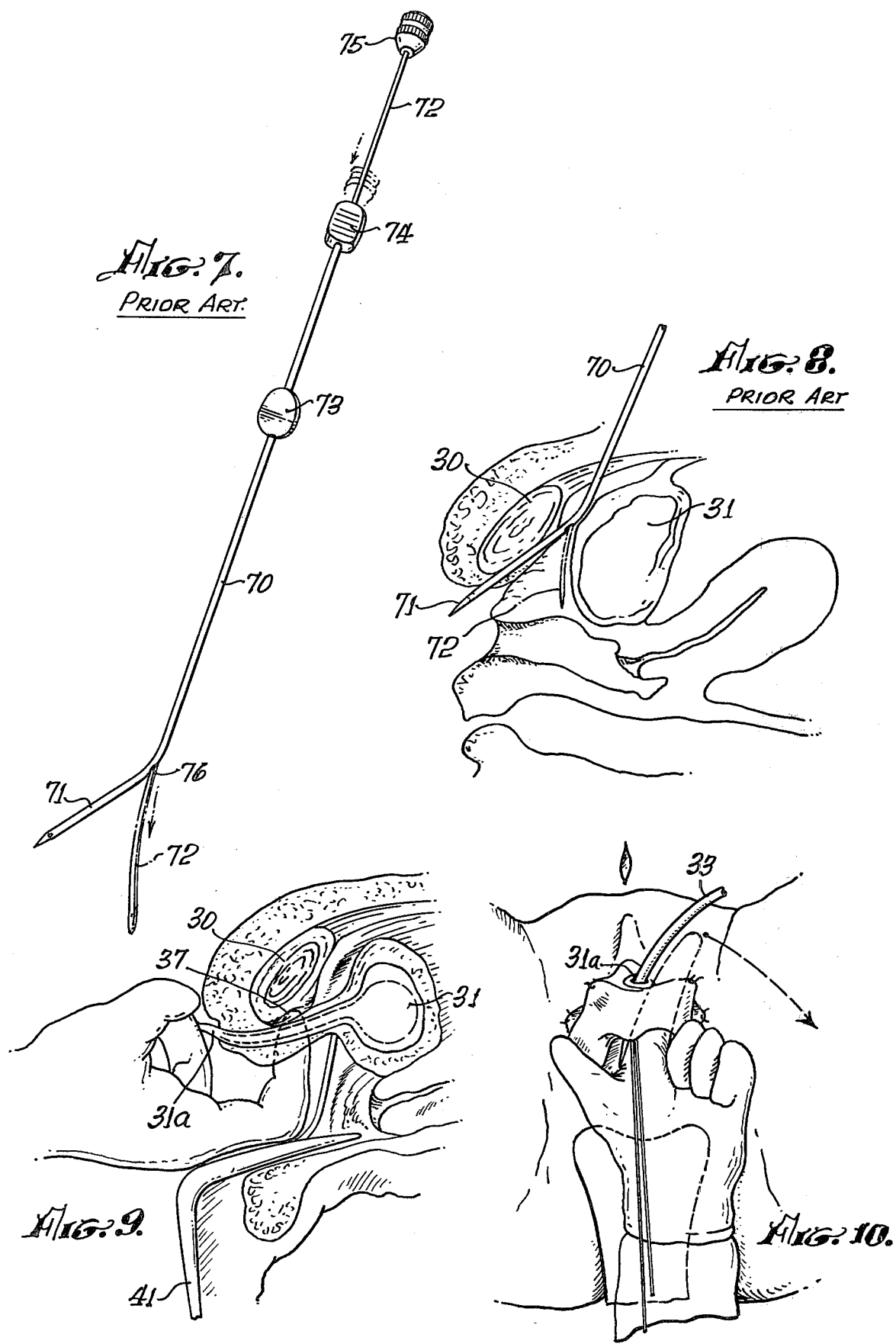

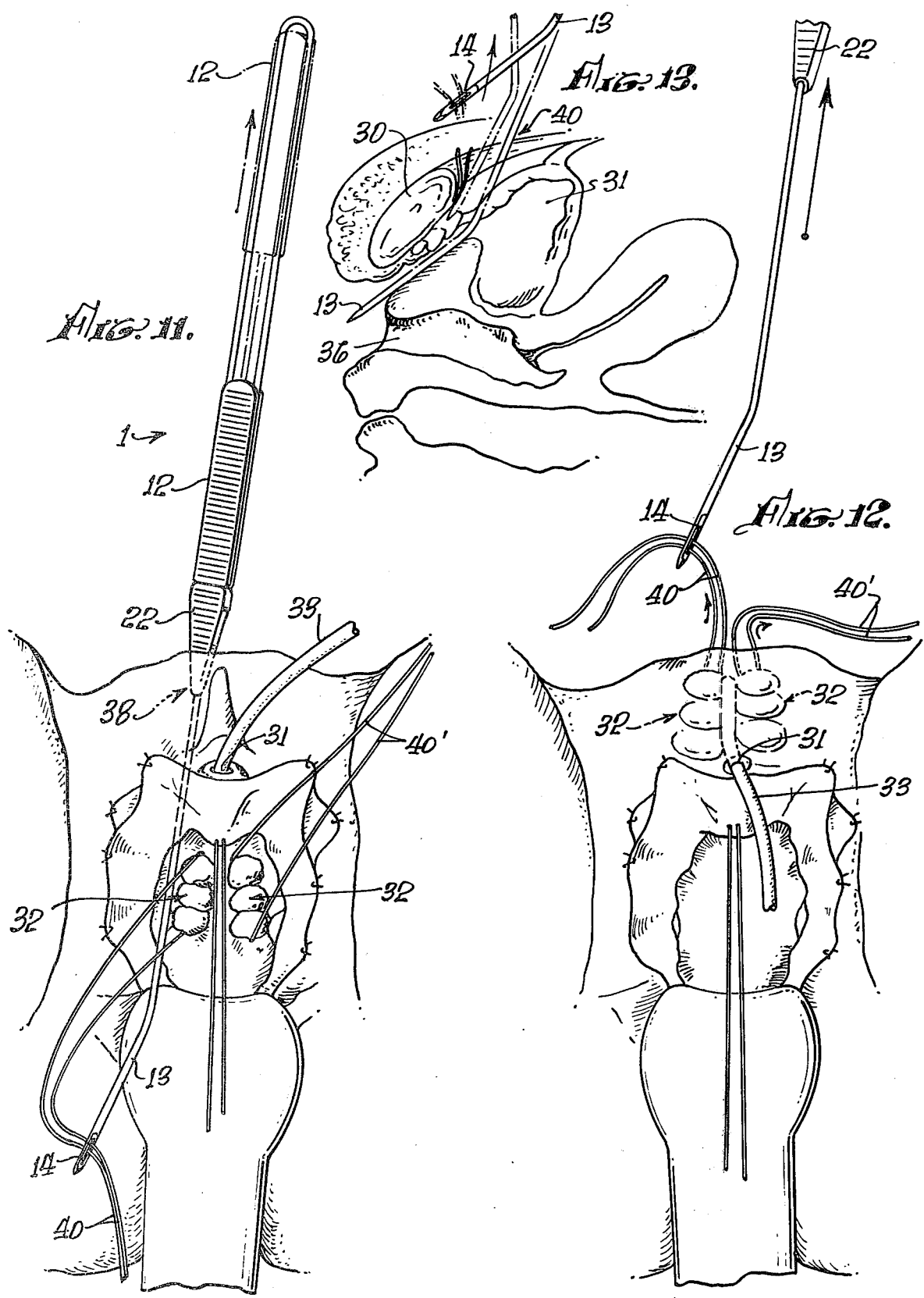

SURGICAL LIGATURE CARRIER

BACKGROUND OF THE INVENTION

1. Field of the Invention

The urethra is a tube about 4 cm long which is normally closely attached by ligamentous and musculofacial tissue supports to the pelvic bone. Its point or union with the bladder, called the urethrovesical (u-v) junction or bladder neck, is located behind the pubic bone; the structure is such that an increase in intraabdominal pressure (as from coughing) will not permit escape of urine through the urethra.

Weakening and stretching of the attachment of the urethra to the pubic bone, which sometimes result from childbirth, may allow the u-v junction to prolapse and cause stress urinary incontinence, the involuntary escape of urine during coughing, sneezing, or other actions producing such stress. This condition is corrected by surgical restoration of the u-v junction to its orthotopic position.

Various operations have been devised to restore the elevation of the bladder neck junction. Their purposes are to restore the junction to its elevated position.

A problem in the Pereyra operation is the need for precise control of the ligature carrier needle, which is inserted through the tough abdominal fascia, advanced down between the posterior pubis and the anterior bladder wall and projected out through the vagina.

1. Discussion of the Prior Art

In a prior operation of this type invented by the present inventor, a ligature carrier of different design was employed with a retractable needle sliding inside an angulated hollow needle. With the first needle extended behind the pubic bone, the presence of two needles therein added to the difficulties of control. The small handles provided did not permit the precise control desirable. This prior device is briefly described and illustrated later herein.

SUMMARY OF THE INVENTION

An improved ligature carrier is provided for retropubic transfer of the suspensory sutures in an improved surgical operation devised by the present inventor and published as the Revised Pereyra Procedure. The operation corrects the condition known as stress urinary incontinence in women by restoring elevation of the prolapsed bladder neck. The weakened, stretched musculofacial tissues holding the urethra to the pubic bone are detached from the pubis and are bound together by a helical suture which is transfixed to the posterior pubourethral ligament on each side of the proximal urethra. The reinforced tissues and ligaments are elevated retropublically through the subpubic openings created by detaching the musculofascial tissues with a ligature carrier of the present invention.

The ligature carrier comprises a brace which guides a retractable needle for extension and retraction. The end of the needle is angulated and contains an eye at its tip. The brace comprises a generally flat serrated or striated brace handle from which parallel guides extend back, away from the needle tip. The body of the single needle slides through a hole in the brace handle. The back end of the needle body is fixed in a needle handle which slides in the guides. The needle handle is flat and striated like the brace handle.

The needle is extended by sliding the needle handle, along its guides, forward toward the brace handle, and retracted by sliding it back to the back limit of the guides. When it is fully retracted the angulated tip protrudes about 3 cm from the brace.

In use, the needle is first retracted, then its tip is pushed through the lower abdominal fascia exposed by an abdominal skin incision. The brace is then suitably reoriented and the needle handle pushed forward so as to extend the needle tip out through the vaginal opening. The ends of the helical sutures previously in place are threaded through the eye of the needle and the instrument withdrawn, bringing the sutures out through the abdominal wall for tying over the abdominal fascia.

BRIEF DESCRIPTION OF THE DRAWINGS

FIG. 1 is a perspective view of a complete ligature carrier according to the invention, with the needle retracted;

FIG. 2 is a view like FIG. 1 but with the needle extended;

FIG. 3 is a partial longitudinal section on Line 3—3 of FIG. 1;

FIG. 4 is a lateral section on line 4—4 of FIG. 1;

FIG. 5 is a lateral section on line 5—5 of FIG. 1;

FIG. 6 is a lateral section on line 6—6 of FIG. 1;

FIG. 7 is a perspective view of a prior art ligature carrier;

FIG. 8 is an anatomical section showing the use of the prior carrier of FIG. 7; and FIGS. 9—13 are anatomical illustrations of steps in an operation using the present invention.

DESCRIPTION OF THE PREFERRED EMBODIMENT

Referring first to FIGS. 1 and 2, the ligature carrier of the invention, indicated generally at 1, comprises a needle 11, 13 which is guided for extension and retraction in a brace or bracket indicated generally at 2. The brace 2 has two major parts: a brace handle body 22 at its lower end and a pair of rod-like guides 20, 20 secured to and extending therefrom.

Mounted in the brace 2 and slidable between and along the guides 20, 20, is a needle handle 12. Fixed in the needle handle 12 is the inner or upper end portion of a suturing needle 11. The needle 11 extends through an opening in brace handle 22 and extends unsupported to terminate beyond the brace 2 in an angulated outer end portion 13. The tip of outer end portion is sharp and has an eye 14.

The brace guides 20, 20 may be made from a piece of suitable wire stock, with a U-bend 21 defining the terminus or limit of retraction. The needle handle 12 is grooved along its side portions to laterally slidably engage the guides 20, FIG. 4. The lower ends of brace guides 20 are rigidly fixed, as by soldering, in the brace handle body 22, FIGS. 3 and 6. The guides 20 may preferably be somewhat larger in diameter than the needle 11, FIG. 5.

Both handles 12 and 22 are preferably of about the same generally flat cross-section so that they form a generally continuous handle in the extended position of FIG. 2. Both are preferably knurled, serrated, or striated on one side only as at 23, FIGS. 2 and 3, to provide a good grip for the operator and to enable the operator to identify the direction of angulation of the needle end while it is submerged in body tissues.

The whole of the instrument is preferably made of stainless steel.

Important features of the invention are:

(a) the brace handle 22 lying near the needle end 13 in retracted position, FIG. 1, to provide good control in penetrating the tough abdominal fascia; (b) the generally flat shape of both handles with striated surfaces on only one side orienting the operator as to the location of the needle tip; (c) the similar sectional shape of both handles; (d) the provision of a single needle; (e) the provision of guides 20, 20 extending back to provide better orientation to the operator on the direction of the needle when it is extended; and (f) the provision of an angulated end to allow upper shaft of instrument to be deflected against the abdomen to keep the sharp, needle tip pointed against the posterior pubic bone and away from the bladder.

FIGS. 7 and 8 show a prior ligature carrier for a prior operation for the present purpose. In FIG. 7, the prior carrier comprises a hollow cannula or needle 70 with an angulated end portion 71. Inside this hollow cannula 70 extends a solid needle 72, which may be extended out through a hole in the side of cannula 70 at 76. The needle 72 is extended by pushing down on knob 75 at the back or upper end of the device. The cannula 70 is held by small handles 73, 74. Referring now to FIG. 8, this prior needle 70 has been inserted through the abdominal wall above the pubic bone 30, shown in section. The extension of the inside needle 72, as shown, passes close to the bladder 31; if the direction of needle 70 is slightly in error, the needle 72 could puncture the bladder, which is indicated at 31.

Referring now to FIG. 9, an early step is indicated in the operation to which the present invention relates. Here the vaginal opening is held open by a retractor 41, and the musculofascial and endopelvic tissues are being dissected free from the pubis 30, the operator keeping a finger against the pubic bone at 37. In FIG. 10, the operator is exposing the retropubic space, the urethra being indicated at 31a. An indwelling catheter is shown in the urethra and bladder at 33. In FIG. 11, the musculofascial tissues and pubourethral ligaments have been gathered up by helical sutures 40, 40, by other means, into three loops on each side at 32, 32. The substantially last step is to bring the ends of sutures 40,40 out through the abdominal wall incision through the opening made by the needle 13 of the invention in the abdominal fascia. FIG. 11 shows the needle 13 inserted and extended, and the ends of a pair of suture 40 threaded through its eye. The needle has been inserted at a central point 38 through the abdominal fascia while retracted, then turned to one side and extended out through the vagina and the sutures 40 run through its eye; the instrument 1 is then withdrawn, pulling the suture ends out on top of the abdomen. The instrument 1 is then reinserted to the other side, laterally, and the other sutures 40' pulled out. When drawn taut, the sutures hold the musculofascial tissues and in pubourethral ligaments in apposition against the posterior pubis.

By the use of the ligature carrier 1, the transfer of the above sutures, which are suspensory sutures used to reinforce the tissues, are brought up back of the pubic bone without danger of injury to the urethra or bladder, because of the close control possible of the position of the needle 11, 13.

When the procedure is started the needle 11, 13 is retracted and only the angulated portion 13 is protruding from the brace handle 22, which gives the operator solid, firm control so he can grasp the instrument close to the needle point and exert the force necessary to introduce the needle end through the tough abdominal fascia without risk of bending the long narrow needle which is protected and supported by the brace. The eye of the needle end then is advanced retropubically down safely past the bladder and out of the vagina without force to pick up the helical suture ends and bring them out through the fascia thus elevating the bound reinforced musculofascial tissues and pubourethral ligaments into proper position to fuse with the posterior pubic bone permanently to correct the stress urinary incontinence.

The Inventor claims:

1. A ligature carrier for suspensory sutures in surgically restoring the elevation of the urethrovesical junction, comprising:
    a brace comprising a brace handle body having a generally central opening,
    guide means secured to said brace handle,
    a needle handle having at least one side portion in lateral slidable engagement with said guide means, and
    a suturing needle having its inner portion secured to said needle handle, said needle extending slidably through said brace handle body opening and having its unsupported outer end portion extending therefrom,
    whereby the outer end portion of said needle is extendable and retractable for predetermined distances from said brace handle body by sliding said needle in said guide means.

2. A ligature carrier as in claim 1, wherein:
    said end portion of said needle is angulated with a sharp point and an eye at its tip.

3. A ligature carrier as in claim 2, wherein:
    said guide means has an upper terminus against which said needle handle abuts to define the maximum retracted position of said needle,
    said angulated end portion of said needle protruding when in said retracted position between about two and six cm out of said brace handle.

4. A ligature carrier as in claim 3, wherein:
    both said handles are generally flat in cross-section.

5. A ligature carrier as in claim 4, wherein:
    the generally flat surfaces of said handles are provided with striations on one side only.
    said side being the side toward which said end portion is angulated.

6. A ligature carrier as in claim 1, wherein:
    said guide means comprises two parallel rod-like members,
    said needle handle having grooves along its opposite narrower sides slidably engaging said rod-like members,
    the flat sides of said needle handle lying in planes parallel to a plane containing said members.

7. A ligature carrier as in claim 6, wherein:
    said rod-like members are formed of a single length of wire stock bent into an elongated U-shape, its open ends fixed into said brace handle and its closed end forming said upper terminus.

8. A ligature carrier as in claim 1, wherein:
    the cross-sectional size and shape of both said handles is substantially the same,
    both said handles lying adjacent and in line when said needle is fully extended and forming a generally continuous combined handle means.

9. A ligature carrier for suspensory sutures in surgically restoring the elevation of the urethrovesical junction, comprising:
- a brace comprising a brace handle having a generally central axial clearance hole,
- axial guide means fixed to said brace handle and having an upper terminus against which said needle handle abuts to define the maximum retracted position of said needle,
- a needle handle supported by and slidable along said guide means,
- said brace and needle handles being generally flat in cross-section,
- the cross-sectional size and shape of both said handles being substantially the same,
- both said handles lying adjacent and in line when said needle is fully extended and forming a generally continuous combined handle means, and
- a suturing needle having its inner end portion fixed in said needle handle and its body portion extending slidably through said clearance hole,
- whereby the outer end portion of said needle is extendable and retractable for predetermined distances outside of said brace handle by sliding said needle in said guide means,
- said outer end portion of said needle being angulated with a sharp point and an eye at its tip, said angulated end portion of said needle protruding when in said retracted position between about two and six cm out of said brace handle.

10. A ligature carrier as in claim 9, wherein:
- said guide means comprises two parallel rod-like members,
- said needle handle having grooves along its opposite narrower sides slidably engaging said rod-like members,
- the flat sides of said needle handle lying in planes parallel to a plane containing said members.

11. A ligature carrier as in claim 10, wherein:
- said rod-like members are formed of a single length of wire stock bent into an elongated U-shape, its open ends fixed into said brace handle and its closed end forming said upper terminus.

* * * * *